United States Patent
Dupuy et al.

(10) Patent No.: US 11,497,554 B2
(45) Date of Patent: Nov. 15, 2022

(54) HEAT SUBSTRATE AND/OR IMAGE ENHANCEMENT COMPOSITIONS AND ENHANCED TISSUE ABLATION METHODS

(71) Applicants: Brown University, Providence, RI (US); Rhode Island Hospital, Providence, RI (US)

(72) Inventors: Damian E. Dupuy, Centerville, MA (US); William Keun Chan Park, Westerly, RI (US); Edward G. Walsh, Danielson, CT (US)

(73) Assignees: Brown University, Providence, RI (US); Rhode Island Hospital, Providence, RI (US)

( * ) Notice: Subject to any disclaimer, the term of this patent is extended or adjusted under 35 U.S.C. 154(b) by 1263 days.

(21) Appl. No.: 15/831,615

(22) Filed: Dec. 5, 2017

(65) Prior Publication Data

US 2018/0153617 A1    Jun. 7, 2018

Related U.S. Application Data

(63) Continuation of application No. PCT/US2016/035995, filed on Jun. 6, 2016.
(Continued)

(51) Int. Cl.
*A61B 18/18*    (2006.01)
*A61B 5/055*    (2006.01)
(Continued)

(52) U.S. Cl.
CPC .......... *A61B 18/1815* (2013.01); *A61B 5/055* (2013.01); *A61K 9/0004* (2013.01);
(Continued)

(58) Field of Classification Search
CPC .............. A61B 18/18; A61B 18/1815; A61B 2018/1861; A61B 2018/1869;
(Continued)

(56) References Cited

U.S. PATENT DOCUMENTS 8,565,892 B2 * 10/2013 Nayfach-Battilana ...................... A61P 31/04
607/103
2003/0028071 A1 * 2/2003 Handy ................. A61N 2/02
600/12
(Continued)

FOREIGN PATENT DOCUMENTS

WO    2014031727 A1    2/2014

OTHER PUBLICATIONS

Brown, DB et al. (2006). "Society of Interventional Radiology position statement on chemoembolization of hepatic malignancies". J Vasc Interv Radiol 17(2): 217-23.
(Continued)

*Primary Examiner* — Ronald Hupczey, Jr.
*Assistant Examiner* — Bradford C. Blaise
(74) *Attorney, Agent, or Firm* — Nutter McClennen & Fish LLP (57) ABSTRACT

Ferritin or iron-based image enhancement agents identify target tissue for treatment or ablation and are heated by microwave absorption. Microwave heat substrates enhance microwave hyperthermal ablation treatment, and may be percutaneously delivered and imaged by x-ray CT during placement of the microwave treatment antenna, allowing more precise positioning and more complete ablation of a tumor site. One method of treating a target tissue uses image-guided delivery of a heat substrate with a reverse-phase change polymer, and may apply energy to fix a mass of the material in the tissue. The fixed polymer may increase
(Continued)

hyperthermia, form a thermal boundary, or blockade a vessel or passage so as to reduce or prevent undesired conductive cooling by contiguous tissue, or may deliver a localized treatment drug at the site, upon heating or as it degrades over time.

14 Claims, 5 Drawing Sheets

Related U.S. Application Data (60) Provisional application No. 62/171,609, filed on Jun. 5, 2015.

(51) Int. Cl.

| | | |
|---|---|---|
| *A61K 41/00* | (2020.01) | |
| *A61K 49/18* | (2006.01) | |
| *A61K 49/04* | (2006.01) | |
| *A61K 33/14* | (2006.01) | |
| *A61K 33/18* | (2006.01) | |
| *A61K 33/26* | (2006.01) | |
| *A61B 5/00* | (2006.01) | |
| *A61N 5/02* | (2006.01) | |
| *A61N 5/04* | (2006.01) | |
| *A61N 5/10* | (2006.01) | |
| *A61K 38/17* | (2006.01) | |
| *A61K 9/00* | (2006.01) | |

(52) U.S. Cl.
CPC ............ *A61K 9/0024* (2013.01); *A61K 33/14* (2013.01); *A61K 33/18* (2013.01); *A61K 33/26* (2013.01); *A61K 38/1709* (2013.01); *A61K 41/0052* (2013.01); *A61K 49/0404* (2013.01); *A61K 49/1818* (2013.01); *A61N 5/025* (2013.01); *A61N 5/045* (2013.01); *A61N 5/10* (2013.01); *A61B 5/0035* (2013.01); *A61B 2018/1869* (2013.01); *A61K 49/04* (2013.01)

(58) Field of Classification Search
CPC .... A61B 5/055; A61K 9/0004; A61K 9/0024; A61K 33/14; A61K 33/18; A61K 33/26; A61K 41/0052; A61K 49/0404; A61K 49/06; A61K 49/1818; A61N 5/025; A61N 5/045

See application file for complete search history.

(56) References Cited

U.S. PATENT DOCUMENTS

| | | | | |
|---|---|---|---|---|
| 2005/0256360 | A1* | 11/2005 | Hainfeld | A61K 41/0052 600/1 |
| 2010/0198210 | A1* | 8/2010 | Lanphere | A61K 47/36 606/28 |
| 2011/0034916 | A1* | 2/2011 | Te | A61N 5/02 606/33 |
| 2011/0105825 | A1* | 5/2011 | Nayfach-Battilana | A61K 41/0052 600/12 |
| 2013/0261710 | A1* | 10/2013 | Won | A61N 5/04 607/100 |
| 2013/0267940 | A1 | 10/2013 | Chiang et al. | |
| 2013/0336897 | A1 | 12/2013 | Wolf et al. | |
| 2017/0182165 | A1 | 6/2017 | Park et al. | |

OTHER PUBLICATIONS

Duan, X, et al. (2014). Heat shock protein 70 expression and effect of combined transcatheter arterial embolization and radiofrequency ablation in the rabbit VX2 liver tumour model. Clin Radiol. 69(2):186-93.

Ginsburg, M et al. (2013). Comparison between transarterial chemoembolization in combination with radiofrequency ablation versus microwave ablation in the management of hepatocellular carcinoma. J Vasc Interv Radiol, 24(4) S43-44 (Abstract available).

Isfort, P et al., (2014) "Efficacy of magnetic thermoablation using SPIO in the treatment of osteoid osteoma in a bovine model compared to radiofrequency and microwave ablation" Cardiovasc Intervent Radil (2014) DOI 10.1007/s00270-013-0832-7.

Mostafa, EM et al. (2008). Optimal strategies for combining transcatheter arterial chemoembolization and radiofrequency ablation in rabbit VX2 hepatic tumors. J Vasc Interv Radiol. 19(12):1740-8.

Ninh, C et al., (2014). Photoresponsive hydrogel networks using melanin nanoparticle photothermal sensitizers. Biomater. Sci., 2, 766-774.

Qian T, et al. (2014). Diffusion-weighted magnetic resonance imaging to evaluate microvascular density after transarterial embolization ablation in a rabbit VX2 liver tumor model. Magn Reson Imaging. 32(8):1052-7.

International Search Report and Written Opinion of the International Search Authority in PCT/US16/35995 dated Oct. 7, 2016 (9 pgs.).

Extended European Search Report for Application No. EP 16804631.6 dated Apr. 17, 2019, 14 pages.

Manthe, R., et al., "Tumor Ablation and Nanotechnology," Molecular Pharmaceutics, vol. 7, No. 6, Dec. 6, 2010, pp. 1880-1898.

Park, W., et al., "Evaluation of a Novel Thermal Accelerant for Augmentation of Microwave Energy during Image-guided Tumor Ablation," Theranostics, vol. 7, No. 4, Feb. 26, 2017, pp. 1026-1035.

Park, W., et al., "A novel thermal accelerant for augmentation of microwave energy during image-guided tumor ablation," Progress in Biomedical Optics and Imaging, SPIE—International Society for Optical Engineering, Bellingham, WA, US, SPIE vol. 10066, Jan. 29, 2017, 3 pages.

\* cited by examiner

FIGURE 1

TABLE 1
Microwave Heating Trial

|  | Sample | Observed Microwave Thermal Response |
|---|---|---|
| Beaker 1 | 10mL H₂O | 10W→20W<br>Slowly went up but a lot of fluctuation |
|  | 10mg CsCl in 10mL H₂O | Fluctuating, slow increase<br>Began to climb steadily at 2:30<br>Final temperature around 38-40°C |
|  | 100mg CsCl in 10mL H₂O | Start temp: 31°C<br>Fluctuating, slowly increasing initially<br>Final temperature: 50°C in 5:22 |
|  | 1g CsCl in 10mL H₂O | Start temp: 32°C<br>Steadily increased with fluctuations<br>Final temperature fluctuating between 56-62°C after 6min |
|  | Ferumoxytol 50mg | Start temp: 29°C<br>Trend was up, but extremely slow and fluctuating a lot<br>Final temperature: 40°C after 6 min |
|  | Ferritin 5mg | Start temp: 27°C<br>Final temperature: 60°C after 5:45 |
| Beaker 2 | 20% polymer in 1mL H₂O | Start temperature: 33°C<br>Gelled up as temperature increased to 40°C<br>Final temperature: 45°C after 6 minutes |
|  | 20% Polymer with 100mg CsCl in 1mL H₂O | Start temperature: 30°C<br>Final temperature: around 80°C in 19-20s<br>Went up so quickly that needed to shut off before it exploded |

HEAT SUBSTRATE AND/OR IMAGE ENHANCEMENT COMPOSITIONS AND ENHANCED TISSUE ABLATION METHODS

RELATED APPLICATIONS

This application is a continuation of international application PCT/US2016/035995 filed on Jun. 6, 2016, which is related to and claims the priority of U.S. Provisional Application 62/171,609 filed on Jun. 5, 2015. Each of these applications, together with its drawings, appendices and attachments is hereby incorporated herein by reference in its entirety.

TECHNICAL FIELD

The present invention relates to nanoparticle-based theranostic methods of imaging and/or treating tissue, such as a tumor or cancerous tissue present in a gland or organ. It also relates to image-guided minimally invasive treatments of such tissue, such as intravascular embolic ablation treatment.

BACKGROUND

Much medical imaging involves imaging modalities that have been developed for gross anatomical applications, such as the detection of internal traumatic events (such as bone fractures or dislocations) by transmission x-ray imaging, or such as detection of soft tissue pathologies by magnetic resonance imaging (MRI) or x-ray computed tomography (CT). In general, x-ray imaging is poorly adapted to discriminating soft tissue features due to the low absorbance of such tissue and the concomitant low level of image contrast, as compared to the high contrast x-ray images produced, for example, by mineralized skeletal features, which have higher absorbance and thus appear with high x-ray contrast. MRI, which depends upon stimulation of magnetic dipoles of underlying molecules and upon detection of signals emitted by the stimulated tissue, is better suited to soft tissue imaging, and can provide tomographic reconstructions of diverse internal soft tissues, organs and other features. Various image enhancement formulations have been developed to further enhance MRI detection of many specific types of tissue or defects therein, for example, to image blood flow, or to detect vessel leaks in the brain.

Recently, much research has been carried out to develop image enhancement agents that will specifically accumulate at and attach to a target feature of interest, such as a liver cancer, so as to render the target feature visible by medical imaging. For example an MRI enhancement agent for parenteral delivery may include nanoparticles, a biocompatible coating and a monoclonal antibody (mAB) that binds the nanoparticle agent to a receptor or a peptide present on or expressed by a specific tumor cell line, so that as the agent circulates it preferentially binds to and accumulates at the target tissue, and thus enables MRI screening for and early detection of such tumors. For some imaging agents based upon nanoparticles, there have been proposals that the nanoparticle further carry a chemotherapeutic treatment cargo, or be engineered to release a toxic residue, and be delivered in a form that can be released at the tissue binding site via application of externally-applied stimulation, such as ultrasonic or electromagnetic stimulation. By using such targeted nanoparticles one can thereby selectively increase the concentration which resides at the intended treatment site, in contact with cancer cells; one can visually confirm both the existence of the type of targeted tissue and confirm the effective delivery of agent at the site, thereby assuring that the chemo cargo directly contacts the specific tissue requiring treatment. See, for example International Application WO 2014/031727 published 27 Feb. 2014, which reports a tissue-targeting engineered ferritin for MRI imaging that is specifically taken up by targeted cells to enable diagnostic imaging, and may be externally stimulated to release a large quantity of toxic iron ions and treat the targeted tissue. That ferritin involves a genetically-engineered ferritin cage derived from *Archaeoglobus Fulgidus* developed by Swift and Sana, as further described in the aforesaid international application.

However, the amount of material that may be carried by nanoparticles to deliver as a treatment agent, or the concentration of nanoparticles that will be result at a tissue site (either for treatment purposes or for image enhancement purposes) may be quite small. Actual binding may depend upon a number of potentially competitive factors, including such factors as the binding specificity, and the rates of cellular uptake or of diffusion, degradation and/or clearance of the agent. When magnetic nanoparticles are to be externally stimulated to heat the contacted tissue, the size, coatings, contents and other aspects of the material which has been optimized in preparing a nanoparticle-based or other imaging agent may limit the amount of energy that can be locally imparted to or transferred by the agent to the tissue site. Moreover, when electromagnetic stimulation is intended to result in hyperthermia, the level of conductive cooling by the surrounding thermal mass or cooling provided by blood circulation may be so large as to effectively prevent energized nanoparticles from increasing the temperature of the targeted tissue features to the necessary ablation threshold, or may require a massive or high-powered magnetic field generator and very technical positioning or adjustment to attain sufficiently elevated local temperatures. Similar factors may strongly limit the achievable level of therapy when the operative mechanism involves stimulating the agent to release material or stimulating the agent to itself locally interact with tissue. One article has reported investigating the use of iron oxide nanoparticles as an accelerant for microwave ablation, but was unsuccessful in a comparison study with RF and magnetic hyperthermia. Isfort et al, Cardiovasc Intervent Radii (2014) DOI 10.1007/s00270-013-0832-7.

It would therefore be desirable to provide a tumor-targeting or image enhancing agent that enables, simplifies, enhances or provides a therapeutic activity.

It would also be desirable to provide an agent that is simple to deliver, free of toxicity, and effective to simplify or improve local treatment, such as microwave or other hyperthermal ablation treatment, of a targeted tumor or tissue pathology.

It would also be desirable to provide simpler, safer or improved methods for treatment of a targeted tumor or tissue pathology, such as thermal or microwave tissue ablation methods.

SUMMARY

These and other desirable improvements are achieved with improved materials and methods of the invention as described further below.

The present invention provides enhanced methods of treating tissue, such as a tumor or cancerous tissue present in tissue, a gland or organ, and operates by providing a heat substrate component or material which may be heated by applying electromagnetic or microwave energy to locally ablate tissue. In various embodiments the invention also provides image enhancement, enhancing visibility of a targeted tissue or feature by CT or MR imaging modalities, and/or allowing image guided delivery of the substrate for treatment. The imaging agent may be adapted to target specific tissues or characteristics of a tumor so as to detect and identify a tumor or early stage cancer and thereby confirm presence of the agent at the tissue site. In embodiments wherein the heat substrate is also an image enhancing agent, it may be externally heatable to enhance thermal ablation of the targeted tissue, for example, to render faster, or more localized or otherwise more effective microwave ablation or electromagnetically stimulated heating of the tissue that has been specifically targeted or contacted by the agent.

In one aspect of the invention, an engineered ferritin is targeted to specific tissues by binding specific ligands to an outer surface of the ferritin cage, and acts as an MRI contrast agent to provide positive identification of the target tissues in which the agent has accumulated. The resultant presence of a high iron concentration enhances the efficacy, e.g., rate of temperature increase, of a microwave ablation procedure, providing an additional capability for such ferritin material to define a treatment region and also reduce damage to surrounding tissue.

In another or further embodiment for enhanced thermal tissue ablation, a heat substrate agent is formulated for direct delivery, for example image-guided delivery by catheter or needle, and includes a reverse phase change carrier gel or polymer that thickens as its temperature is increased, or that solidifies at or near body temperature, fixing the substrate and/or hardening the polymer at the delivery site. When injected into a passage such as a duct or the arterial tree of a target tissue mass, solidification blocks the passage, closing off circulatory cooling and thereby lowering the effective thermal mass of the target tissue, and increasing the effective rate or endpoint of tissue heating in the mass as a whole. Solidification may be assured by providing a reverse phase change material that solidifies at body temperature; alternatively, solidification may also be accelerated by applying energy to the heat substrate to quickly reach the transition temperature. The reverse phase change polymer advantageously enables a treatment modality (such as magnetic excitation to heat a nanoparticle agent) which might otherwise be ineffective at transferring sufficient heat to raise the contacted tissue to an ablation level in the local area. For certain tissue structures, rather than blocking ducts or vessels, the heatable reverse phase change polymer may also be delivered to surround and enclose a tissue target in a heat sheath, or to install a bounding thermal wall of material that overcomes or limits the amount of undesired conductive cooling that would otherwise occur. At higher temperatures the polymer can solidify and expel therapy agents into the contiguous tissue or tissue structure, or release a therapeutic agent at the target site over an extended time as the material breaks down.

In various embodiments, heating of the heat substrate may be accomplished by externally applying an alternating electromagnetic field (for example to heat a substrate, such as a ferritin-based or other iron oxide-based treatment or imaging agent containing iron or $Fe_3O_4$) or heating may be effected by applying microwave energy to the treatment or imaging agent. The presence of iron (as engineered ferritin nanoparticles providing enhanced contrast effect for imaging, or as ferumoxytol for iron replacement therapy) enhances the tissue heating and thus the tissue sensitivity to microwave heating, or heating by electromagnetic stimulation. Targeted MRI image enhancement to identify specific tissue sites may be effected using iron-laden engineered ferritin nanoparticles carrying monoclonal antibodies to bind to sites of the specific targeted tissue, or sites may be marked by image-guide delivery of an agent such as the iron-replacement agent ferumoxytol to the intended site. As noted above, the ferritin or ferumoxytol may also serve as heat substrate for thermal tissue ablation. The reverse-phase transition polymer need not itself include image-enhancing components, but may be placed by image-guided delivery and then independently heated to quickly block circulation or immobilize the material at the site once the target has been identified.

Unlike chemotherapy injections which can diffuse away from the site of injection the iron nanoparticle/polymer becomes a gel and thus localizes to where it is injected. The iron oxide matrix within the gel can be dose dependently heated to the cytotoxic threshold via interstitial or extracorporeal excitation by a radiofrequency field (e.g microwave). The iron oxide/gel combination may also act as a contrast agent allowing for image-guided delivery and verification of the volume occupied by the gel.

Existing thermal ablation techniques used to treat cancerous tumors have a high local recurrence rate (~40%) which is, in part due to the cooling effect of blood vessels. Blocking the blood vessels with the iron nanoparticle/polymer will achieve two purposes: reducing tumor blood flow (thus mitigating any cooling effects of flowing blood) and allowing localized thermal energy delivery through the excitation of the local iron oxide within the polymer, via interstitial or extracorporeal excitation. Current liver tumor directed therapies through the arterial tree rely on chemotherapy emulsions, drug-eluting beads or radioactive beads that are expensive and only rely on the toxic effects of the drug or the ionizing radiation. The iron oxide nanoparticle/polymer of the present invention is a more cost effective formulation and has a higher safety profile because the components are readily broken down and metabolized within a few weeks.

The inventors have further identified a non-iron agent useful as a heat substrate that is both imageable and effective for microwave thermal ablation, namely cesium chloride (CsCl). This heat substrate may be added to the agent or to a reverse-phase transition polymer as an ingredient to substantially accelerate heating and solidification of the polymer, or may be delivered to the tissue itself to enhance heating and ablation of the tissue using a percutaneously placed microwave antenna. The CsCl material is also CT imageable, and thus supports additional image-guided microwave therapies.

Various other agents may be used to enhance ablation by increasing the coefficient of microwave absorption, allowing faster heating, lower power, and more effective tumor ablation via minimally invasive procedures using a conventional microwave surgical instrument. In embodiments of the invention and methods of treatment, the targeting agent, the polymer heating agent, and the tumor sensitizing agent may be different materials, and their size, form, concentration or other attributes may be individually optimized for different properties, such as (1) targeting and imaging the tumor by CT or MRI; (2) placing and quickly heating, by electromagnetic or microwave stimulation, the blocking gel to a solid state to reduce circulatory cooling of the imaged tumor; and (3) heating the tumor-bound or tumor-binding agent sufficiently to ablate the tissue to which the targeted agent is fixed.

BRIEF DESCRIPTION OF THE DRAWINGS

These and other features of the invention will be understood from the drawings and the description herein, taken together with the above-cited International Application WO 2014/031727 published 27 Feb. 2014 which is hereby incorporated herein in its entirety by reference. The drawings, description, cited paers and claims, infra, describe methods and materials of the invention and intended variations and extensions thereof, together with certain representative and proof-of-principle measurements and experiments, wherein

DETAILED DESCRIPTION

The invention may be viewed as an advance in image-guided thermal ablation (IGTA), a conventional treatment which uses needle-like applicators to deliver energy into tumors and cause instantaneous cell death. Aspects of the invention also promise improved ablation or heating characteristics for treating tumors or isolated metastatic tissue portions that have been targeted with imageable theranostic preparations, such as image enhancement preparations containing mAB-targeted ferritin nanoparticles as described in the aforementioned International Application WO 2014/031727 and technical papers referenced therein. Some embodiments involve heat-mediated release of a treatment agent. A central discovery behind the improved tissue ablation procedures and materials described herein is the realization that iron-loaded imaging agents and theranostic preparations such as the aforesaid ferritin or iron oxide preparations are efficient absorbers of microwave radiation, and may be employed for, or further enhanced for carrying out, processes of microwave hyperthermal ablation, localized fixation and drug delivery, and also enhanced imaging of treatment processes.

Figure 1:
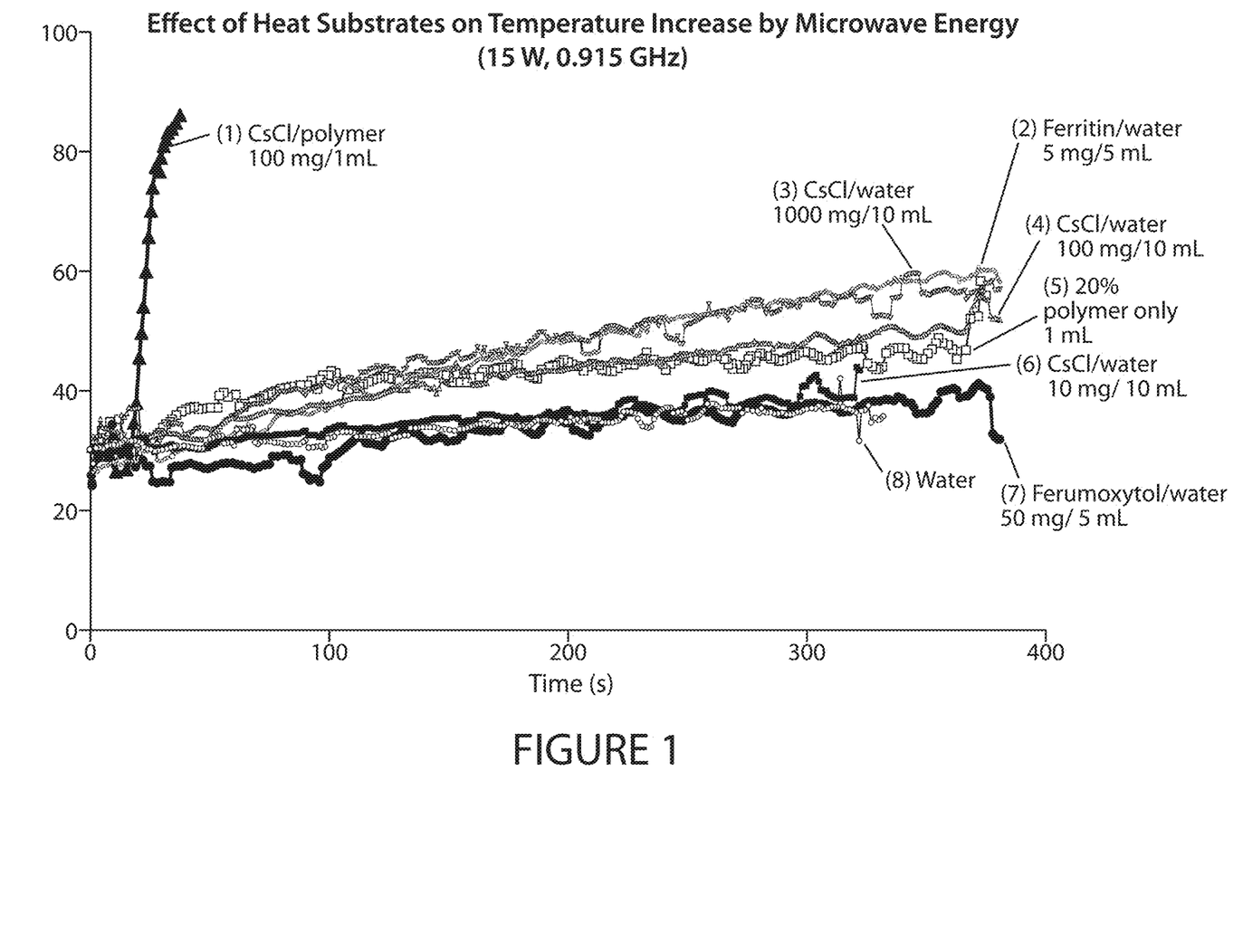
FIG. 1 is graph of temperature increases observed with several heat substrate agents using low power microwave stimulation.

FIG. 1 illustrates microwave heating and heat transfer characteristics of several iron-based formulations, as well as the non-iron material cesium chloride which is identified herein as an effective and useful microwave-absorbing heat substrate, and polymer formulations.

Microwave heating was carried out using a 15 watt 0.915 gigaherz microwave source directed at a vial of each preparation, and the resulting temperature rise was plotted over the course of approximately six minutes. Increasing concentrations of cesium chloride in water resulted in increased heating; similar microwave heating characteristics are expected for cesium iodide.

Figure 2:
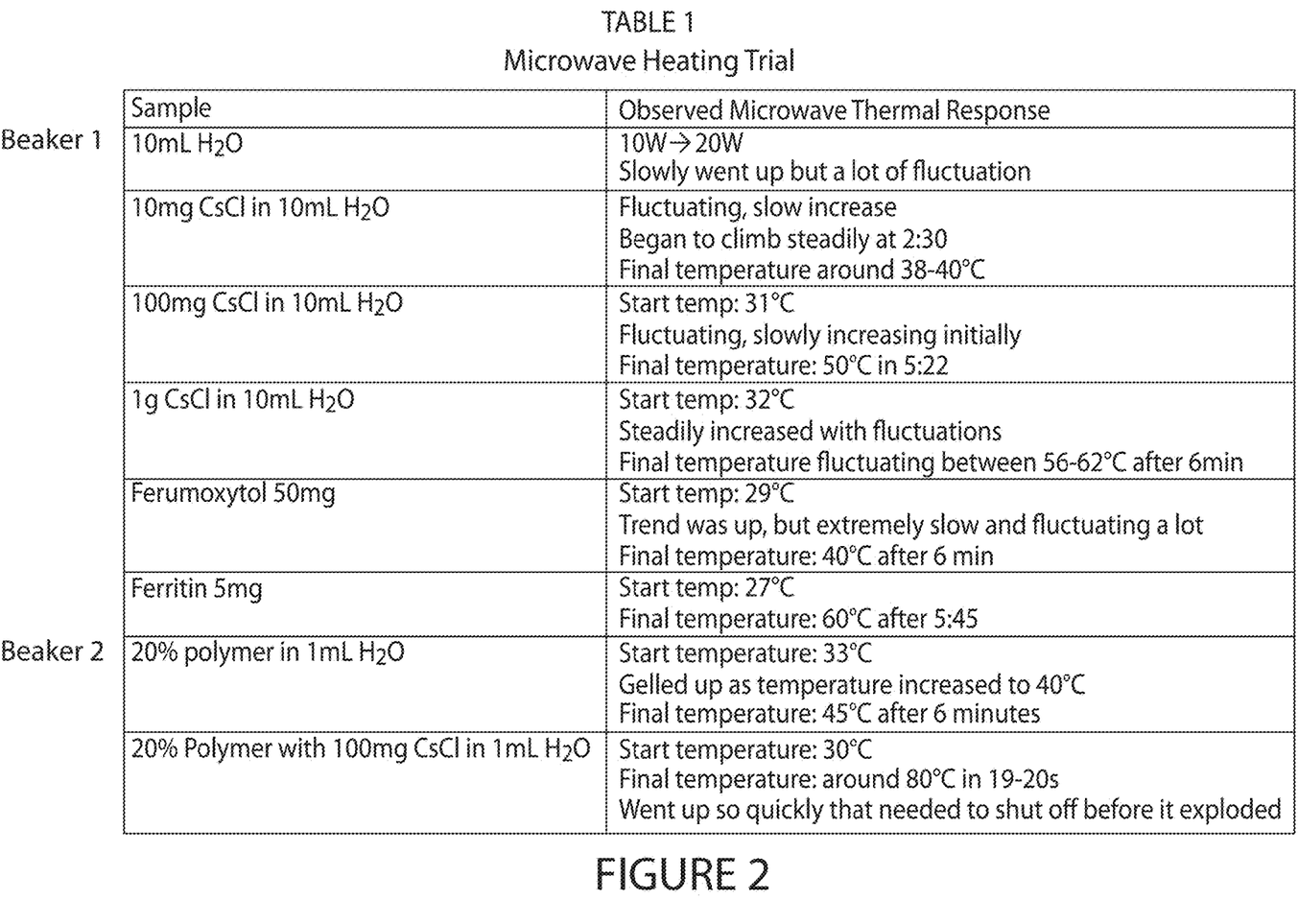
FIG. 2 is a chart showing effective temperature and heating profiles with several iron-based formulations, CsCl concentrations and polymer in vitro.

FIG. 2 is a Table summarizing the effective heating and endpoints achieved with various concentrations of the indicated materials in small sample vials located in a beaker of soft agar. The beaker provides a consistent external temperature surround so as to closely model expected heat transfer and temperature increase profiles that would be expected in the body under the applied levels of microwave heating. The microwave energy was 15 W for all but the first sample, for which various power levels were applied to assess heating of a plain water control, and for all samples was a 915 MHz microwave signal, which was applied with a coaxial dipole antenna of construction similar to that used for clinical therapy, e.g., a needle-like microwave applicator. Ferritin, the iron oxide formulation Ferumoxytol and polymer each displayed useful microwave heating characteristics, and cesium chloride solutions achieved higher temperature increases, while cesium chloride in polymer resulted in such a fast temperature rise that it needed to be shut off before an explosion could occur. These tests established that the iron-based agents, in addition to the polymer, possessed suitable microwave absorption characteristics, so that the imaging agents could also be used for microwave hyperthermal ablation of the imaged tissue. The tests also established that addition of cesium chloride in suitable concentrations would enhance the ablation efficacy.

Figure 3A:
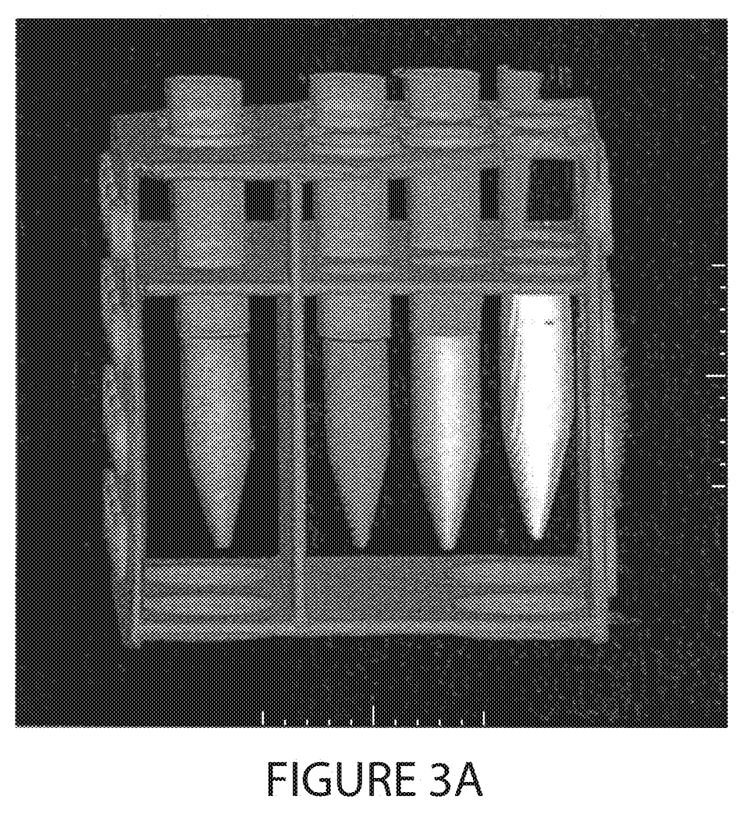
FIGS. 3A, 3B and 3C illustrate CT imaging characteristics of a cesium chloride heat substrate revealing its dual utility for microwave heating and x-ray imaging.
Figure 3B:
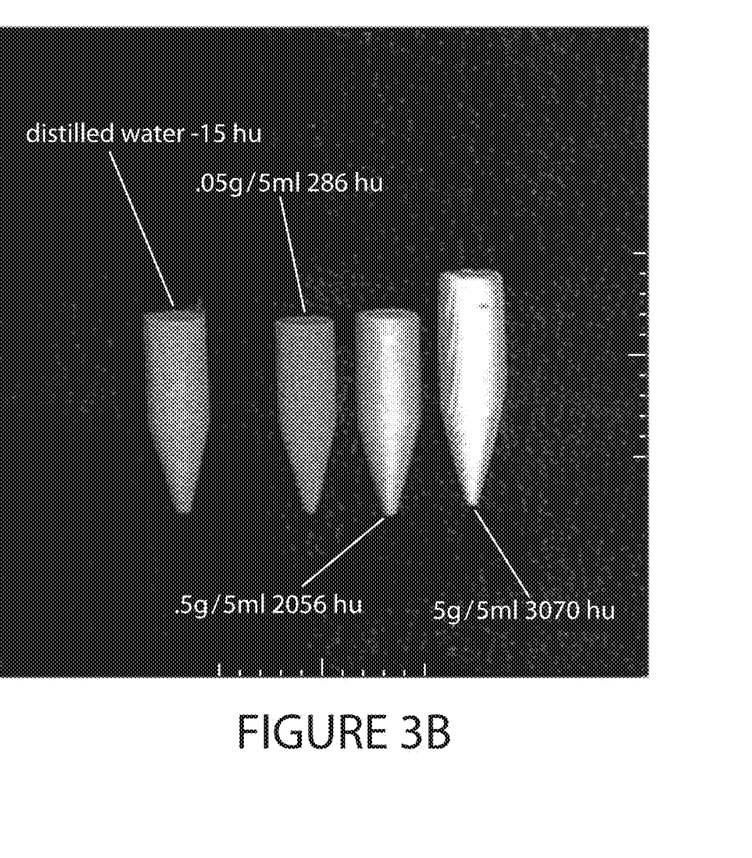
Figure 3C:
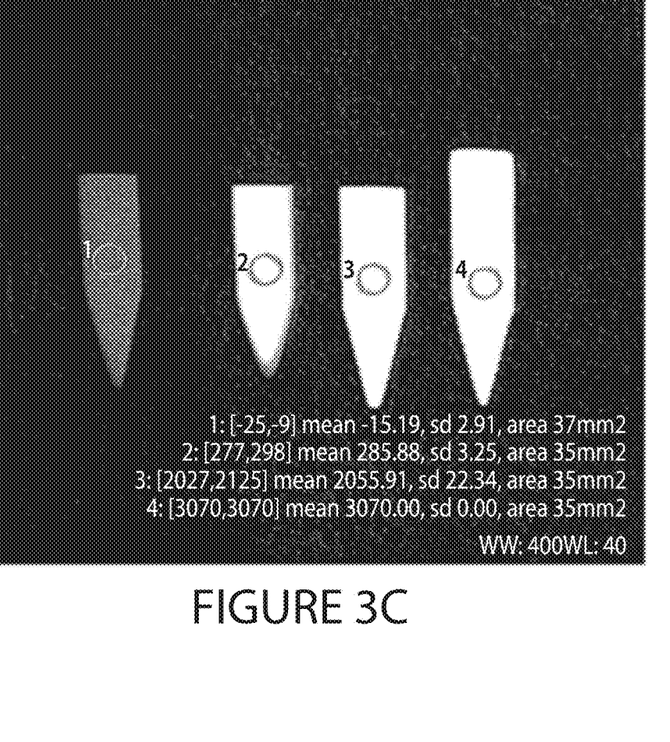

It was further determined that CsCl in relevant concentrations is itself readily imaged in CT devices. Small vials of distilled water and of various concentrations of CsCl were placed in a jig as shown in FIG. 3A and imaged with a GE Optima 580W CT scanner, using a brain CT protocol: 120 kV, 50 mA, 0.8 second rotation, 0.562 pitch and 16×0.625 detector configuration. The radiation output (CTDlvol) was 12.08 mGy, Dose Length Product was 193.88 mGy-cm. The images were evaluated to determine the radiodensity in Hounsfield units. FIGS. 3B and 3C display the radiographic images and the radiodensities, establishing that a range of salt concentrations are suitable for x-ray imaging. Thus cesium chloride (as well as cesium iodide) can be both an effective microwave heat substrate as well as an x-ray CT contrast agent.

Thus for the methods claimed herein, the cesium salt may be imaged by CT, and heated by microwave energy, and the iron-based heat substrate materials may be imaged by MRI or other means, and heated by applying electromagnetic or microwave energy. These properties advantageously are applied herein to provide enhanced imaging and treatment protocols.

FIGS. 3A-3C thus illustrate effective CT imaging of various concentrations of CsCl solution, demonstrating suitability of this material for the heat substrate compositions and image-guided thermal ablation methods described herein.

Image guided thermal ablation (IGTA) is a safe, low-cost, minimally invasive method that can treat numerous tumor types, and is often an alternative to surgical resection. However, while IGTA is effective for local treatment and palliation of symptoms, high treatment variability may be expected when targeting heterogeneous tissue and tumor types, and raises concerns. The present invention instead uses a drug-device combination to improve local control such as localization and effectiveness of heating and, in some embodiments, more effective or precise delivery to a tumor site, so as to improve patient outcomes and broaden the utility of such directed thermal therapy. Specifically, rather than the conventional use of ultrasound to position a microwave ablation antenna, the heat substrates and imaging agents described herein further enable CT imaging of percutaneous microwave ablation procedures and enhanced hyperthermic response of the identified tissue sites.

One further aspect of the invention may utilize the local tissue heating effects of electromagnetic or microwave treatments by reducing blood flow, by means of arterial blockade in the treated or thermally-communicating/proximate tissue. Blockade may be effectively achieved in a thermal ablation methodology that employs a polymer and a heat substrate. The term heat substrate herein refers to a material that may be heated in situ by an applied field, such as an alternating magnet field of suitable strength and frequency, or such as a microwave field (which may be applied with a conventional microwave ablation setup or hand piece—e.g, a needle-like antenna).

As described above, these heat substrates may include iron oxide-nanoparticle material ($Fe_3O_4$—Np, e.g., ferumoxytol or an engineered ferritin.) which in certain embodiments may be presented in an imaging enhancement agent and/or a treatment agent. Heat substrates may alternatively include other materials that have high efficiency for absorbing the applied energy, e.g., microwave or electromagnetic radiofrequency field, and generating heat. As described above, cesium chloride has been found to substantially accelerate heating under low (15 W) applied microwave power, and also to provide CT contrast, and is thus another suitable heat substrate that provides imageability as well as improved heating during microwave ablation.

In addition to augmentation by blockade, local tissue heating effects may in some embodiments also be achieved by placing polymer/ferumoxytol or engineered ferritin nanoparticles into tumors percutaneously, intraductally, or intravenously with specific antibody-targeted delivery. Further enhancements are achieved by combining these heat substrate components with a biodegradable reverse-phase transition polymer, to operate as an embolization medium or a local fixation/delivery mechanism. Once injected, the solution becomes gel-like and heats via a non-invasive, extracorporeal, or interstitial applied energy field. The methodology targets an exact ablation volume and provides a controllable, uniform ablation temperature. Unlike chemotherapy, which can diffuse from the injection site, the heat substrate/polymer localizes to the site. The iron oxide/gel combination, or CsCl/gel also acts as an imaging or contrast agent, allowing for image-guided delivery and verification of the volume occupied by the gel, and these are expected to be highly cost effective and safer than prior treatment protocols not involving blockade because components are metabolized within weeks.

Several points of innovation merit specific mention. First, the combination of heat substrate and polymer creates a suspension where the applied external electromagnetic field or percutaneous microwave field heats the material uniformly. Second, the biphasic polymer becomes gelatinous at body temperature and localizes at the injection point. Third, the polymer may be one that solidifies and expels liquid at temperatures consistent with ablation procedures. Fourth, the polymer/heat substrate combination is viewable under magnetic resonance imaging or CT imaging so localization can be verified prior to electromagnetic or microwave excitation. Finally, the polymer with appropriate characteristics may be one such as a block-co-polymer consisting of polyethylene glycol, which is covalently esterified by an FDA-approved poly lactic-co-glycolic acid on both ends. For ferumoxytol as the iron-based heat substrate, a standard dose is two intravenous administrations of 510 mg (Fe content) over eight days. For this application, ferumoxytol (5-10 mg, Fe content), currently used to treat iron deficiency anemia in adult patients with chronic kidney disease, may be dissolved in the polymer solution (<100 μL) per tumor volume (<1 $cm^3$), which is 50 to 100 times less than a clinical dose. The heat substrate being trapped in a gel that slowly releases the iron oxide, mitigates or effectively reduces the risk of any significant toxicity, thus providing low-dose but highly effective treatment.

The improved tissue imaging and localized tissue heating of the invention should provide better treatment for hepatocellular and other carcinomas. Hepatocellular carcinoma is the fifth most common malignancy worldwide. In addition, the liver is the most common metastatic site of colorectal cancer: the second most common cause of cancer-related deaths in the United States. Current liver-directed therapies have been largely applied as palliative measures—some at high cost—with high recurrence rates. If hepatic disease burden were to be lessened by this less toxic and more cost-effective means, patient costs should be reduced substantially. Thus, $Fe_3O_4$—Np block co-polymer, or CsCl reverse phase change polymer blockade by image-guided delivery, both have great treatment potential in this large group of patients.

Methods of the invention employ an electromagnetic (EM) field or microwave source as the energy source and a combination of ferumoxytol ($Fe_3O_4$—Np) or CsCl, and a biodegradable reverse-phase transition polymer solution as a heat substrate for blockade. The polymer solution is a liquid at ambient temperature, but a gel at typical body temperature (35 to 37 degrees Celsius). Upon a further increase in temperature, the polymer precipitates by expelling water molecules from the polymeric lattice structure while nanoparticles are still trapped.

This expulsion effect is advantageously utilized in an embodiment of the invention as a mechanism for delivering a therapy agent from the fixed polymer/heat substrate body. The $Fe_3O_4$-nanoparticles (Nps) are coated with a polycarbohydrate molecule (a cross-linked dextran with non-reducing end, decomposition temperature less than 240 degrees Celsius) so as to be hydrophilic and, thus, miscible with the aqueous polymer solution. The homogeneous distribution of $Fe_3O_4$—Np in the polymer solution permits uniform heating within the target ablation volume. With image-guidance like CT or MRI, the desired solution volume with a known $Fe_3O_4$—Np (or CsCl) concentration is deposited in and around the tumor or other tissue target. Subsequently, the injected polymer containing $Fe_3O_4$—Np or CsCl turns into a gel of predetermined ablation shape and volume. $Fe_3O_4$—Np in the gel may then be heated by a non-invasive EM field produced by an inductive EM generator, or interstitial microwave energy may be applied to heat the CsCl substrate. The temperature is controlled and ablation optimized by varying several parameters: duration (minutes), electric current (A), power (kW), and frequency (kHz), the iron and cesium concentration (mM), and ablation volume ($cm^3$). The exact iron and cesium concentration of the intra-arterial and directly injected compound, along with the EM field and MW parameters to optimize the efficacy of tumor heating, may be determined by routine experimental assay, calibration and adjustment before application to patients in vivo.

Historically, transcatheter arterial chemoembolization (TACE) and thermal ablation procedures have been most widely applied to hepatocellular carcinoma patients who are not eligible for surgery. Initial implementation and evaluation of the methodology described herein may be carried out and efficacy confirmed with TACE, microwave ablation (MWA), and direct intra-tumoral injection using an animal model, such as rabbit VX2 liver tumor model. A dose escalation study can identify the optimal iron concentration in the $Fe_3O_4$/polymer solution for intrarterial and direct injection and the optimal power and time settings of electromagnetic activation (EMA). After iron concentration and EMA parameter optimization, live animal studies may be undertaken along the route to evaluate and qualify the method for clinical use. For animal studies, a 3T MRI imaging unit can be used to monitor the distribution of the $Fe_3O_4$—Np/polymer solution as well as treatment effects within the liver and liver tumors. Histopathologic analyses including viability staining would preferably also performed to assess vascular thrombosis, necrosis, and tumor viability.

As described herein the thermal substrate properties of engineered ferritin and other iron-based nanoparticle agents, and the demonstrated characteristics of ordinary CsCl as a thermal substrate together with its imageabiliy by several common healthcare imaging systems, amply support the efficacy of the improved, low-cost and safe treatment methods and image-based diagnostic methods, as well as new useful compositions for carrying out the methods described herein. In addition, simple screening methods may quickly identify additional inorganic salts or small molecules with suitable properties to form heat substrate materials with enhanced safety and heating characteristics. Reference is made to the U.S. provisional patent application of which priority is claimed and the appendices thereto, as well as the above mentioned international patent application WO 2014/031727, as well as to various technical papers useful for understanding or preparation of photothermal and reverse phase gel or polymer preparations, including the following papers: Ninh, C., Cramer, M., Bettinger C J., (2014). Photoresponsive hydrogel networks using melanin nanoparticle photothermal sensitizers. *Biomater. Sci.*, 2, 766-774; Brown D B, Geschwind J F, Soulen M C, Millward S F, Sacks D (2006). "Society of Interventional Radiology position statement on chemoembolization of hepatic malignancies". *J Vasc Intery Radiol* 17(2): 217-23; M. Ginsburg, T. Doshi, A. Miller, T. Robbins, R. Kunnavakkam, L. H. Kang, T. VanHa. (2013). Comparison between transarterial chemoembolization in combination with radiofrequency ablation versus microwave ablation in the management of hepatocellular carcinoma. *J Vasc Intery Radiol,* 24(4) S43-44; Qian T, Chen M, Gao F, Meng F, Gao X, Yin H. (2014). Diffusion-weighted magnetic resonance imaging to evaluate microvascular density after transarterial embolization ablation in a rabbit VX2 liver tumor model. *Magn Reson Imaging.* 32(8):1052-7; Duan X, Zhou G, Zheng C, Liang H, Liang B, Song S, Feng G. (2014). Heat shock protein 70 expression and effect of combined transcatheter arterial embolization and radiofrequency ablation in the rabbit VX2 liver tumour model. *Clin Radiol.* 69(2):186-93; and Mostafa E M, Ganguli S, Faintuch S, Mertyna P, Goldberg S N. (2008). Optimal strategies for combining transcatheter arterial chemoembolization and radiofrequency ablation in rabbit VX2 hepatic tumors. J Vasc Intery Radiol. 19(12):1740-8. The foregoing documents and papers are all hereby incorporated herein by reference.

The invention being thus described, variations, and modifications thereof will occur to those of ordinary skill in the art, and all such variations and modifications are considered to be within the scope of the invention and the claims appended hereto.

The invention claimed is:

1. A tissue-targeting theranostic method comprising:
    administering to a patient an engineered ferritin or iron-based nanoparticle formulation having a given temperature at administering, the nanoparticle formulation having a surface functionalized for tumor- or tissue-specific targeting and having iron content that allows MRI imaging to confirm existence of a target tissue and presence of an agent at a target site, and
    after administering the nanoparticle formulation, heating the nanoparticle formulation with microwaves to increase the temperature of the nanoparticle formulation substantially uniformly beyond the given temperature, the nanoparticle formulation being coated at least in part with a poly-carbohydrate molecule such that the nanoparticle formulation is hydrophilic and miscible with an aqueous polymer solution, the nanoparticle formulation including a cross-linked dextran with a non-reducing end or a decomposition temperature less than 240 degrees Celsius, wherein the nanoparticle formulation is configured to turn into a gel of predetermined ablation shape and volume after being administered to the patient;
    locally applying a microwave heat substrate to enhance hyperthermal ablation of the target tissue;
    contacting the target tissue with a flowable or a conformable heat substrate composition that heats up and solidifies when energized by electromagnetic or microwave energy applied thereto,
    applying magnetic field or microwave energy to fix the conformable heat substrate composition as a body in a defined position for enhancing heat transfer to the target tissue, and
    applying further alternating magnetic field or microwave energy to ablate the target tissue.

2. The method of claim 1, wherein the step of heating the nanoparticle formulation with microwaves includes applying microwave energy via a percutaneous microwave ablation probe positioned in the vicinity of the target tissue.

3. The method of claim 1, wherein the microwave heat substrate is a material imageable by x-ray CT.

4. The method of claim 1, further comprising image-guided delivery of a fixable heat substrate positioned to enhance hyperthermal microwave ablation of the target-tissue.

5. The method of claim 4, wherein the fixable heat substrate includes a reverse change polymer that fixes the agent at the target site for sustained and localized delivery of the agent.

6. The method of claim 5, wherein the reverse change polymer comprises a treatment material, and wherein microwave heating or body temperature fixes the treatment material at the target site as a thermal boundary on the target tissue for enhanced ablation.

7. The method of claim 6, wherein the fixable heat substrate including the reverse change polymer fixes the nanoparticle formulation to the target tissue so as to deliver the treatment material over time as the fixable heat substrate is degraded in position.

8. The method of claim 1, wherein the microwave heat substrate enhances microwave energy absorption, such that applying microwave energy to a region of the target tissue elevates temperature of the microwave heat substrate and thermally ablates the target tissue, wherein the microwave heat substrate exponentially increases microwave heating so as to effectively ablate the target tissue; or wherein the microwave heat substrate is delivered into or surrounding the target site to elevate temperature forming a thermal boundary thereby enhancing treatment of the target tissue.

9. The method of claim 1, wherein the conformable heat substrate composition includes engineered ferritin, ferumoxitol, CsCl or CsI.

10. The method of claim 9, wherein ablation of the target tissue is optimized by varying one or more of duration, electric current, power, frequency, iron or CsCl concentration, or ablation volume.

11. A tissue-targeting theranostic method comprising:
    administering to a patient an engineered ferritin or iron-based nanoparticle formulation having a given temperature at administering, the nanoparticle formulation having a surface functionalized for tumor- or tissue-specific targeting and having iron content that allows MRI imaging to confirm existence of a target and presence of an agent at a target site, and after administering the nanoparticle formulation, heating the nanoparticle formulation with microwaves to increase the temperature of the nanoparticle formulation substantially uniformly beyond the given temperature, the nanoparticle formulation being coated at least in part with a poly-carbohydrate molecule such that the nanoparticle formulation is hydrophilic and miscible with an aqueous polymer solution, the nanoparticle formulation including a cross-linked dextran with a non- reducing end or a decomposition temperature less than 240 degrees Celsius, wherein the nanoparticle formulation is configured to turn into a gel of predetermined ablation shape and volume after being administered to the patient;

locally applying a microwave heat substrate to enhance hyperthermal ablation of the target tissue;

contacting the target tissue by image guided catheter delivery of a flowable or a conformable heat substrate composition including a reverse-phase change polymer that thickens or solidifies at body temperature to thereby fix a mass of the flowable or the conformable heat substrate composition at the target site, and applying electromagnetic energy or microwave energy to heat the mass and thereby more effectively achieve thermal ablation of the contacted target tissue and/or deliver a drug from the mass to the target tissue.

12. The method of claim 11, wherein the flowable or the conformable heat substrate composition includes CsCl delivered under x-ray image guidance, and the flowable or the conformable heat substrate composition is heated by microwave energy to ablate the target tissue and/or to expel a therapy drug at the tissue.

13. The method of claim 11, wherein the flowable or the conformable heat substrate composition includes engineered ferritin or ferumoxitol, and the flowable or the conformable heat substrate composition is energized by electromagnetic energy or by microwave energy to thermally ablate the target tissue and/or expel a therapy drug at the target site.

14. The method of claim 11, wherein the reverse-phase change polymer solidifies by expelling water molecules from a polymeric lattice structure while the nanoparticle formulation remains in a fixed position.

* * * * *